US009322820B2

(12) United States Patent
Blick et al.

(10) Patent No.: US 9,322,820 B2
(45) Date of Patent: Apr. 26, 2016

(54) SYSTEM AND APPARATUS FOR NANOPORE SEQUENCING

(71) Applicant: Wisconsin Alumni Research Foundation, Madison, WI (US)

(72) Inventors: Robert H. Blick, Madison, WI (US); Eric James Stava, San Diego, CA (US)

(73) Assignees: Wisconsin Alumni Research Foundation, Madison, WI (US); Universitaet Hamburg, Hamburg (DE)

( * ) Notice: Subject to any disclaimer, the term of this patent is extended or adjusted under 35 U.S.C. 154(b) by 469 days.

(21) Appl. No.: 13/828,230

(22) Filed: Mar. 14, 2013

(65) Prior Publication Data
US 2014/0266147 A1    Sep. 18, 2014

(51) Int. Cl.
*G01N 27/00* (2006.01)
*G01N 33/487* (2006.01)
*G01N 15/12* (2006.01)

(52) U.S. Cl.
CPC .......... *G01N 33/48721* (2013.01); *G01N 15/12* (2013.01); *G01N 15/1218* (2013.01); *G01N 15/1227* (2013.01)

(58) Field of Classification Search
CPC ............ G01N 33/48721; G01N 27/00; G01N 27/3273; C12Q 2565/631; C12Q 2565/607; C12Q 2565/629; C12Q 1/6869; Y10T 29/42; Y10T 29/49; Y10T 29/49002; Y10S 977/924; B03C 2201/18
USPC ........ 324/71.1, 662, 671, 693, 699, 716, 727; 435/287.1–287.2; 977/832, 837–838
See application file for complete search history.

(56) References Cited

U.S. PATENT DOCUMENTS

| | | | | |
|---|---|---|---|---|
| 3,741,627 | A | | 6/1973 | Haertling et al. |
| 4,220,916 | A | | 9/1980 | Zimmermann et al. |
| 4,999,582 | A | * | 3/1991 | Parks ................. G01N 27/3273 204/406 |
| 6,706,203 | B2 | * | 3/2004 | Barth ................. B01D 67/0058 216/33 |
| 6,843,281 | B1 | * | 1/2005 | Barth ..................... B01D 19/00 137/803 |
| 7,077,939 | B1 | * | 7/2006 | Crooks .............. B01D 67/0062 137/1 |
| 7,132,837 | B1 | * | 11/2006 | Tao ........................ G01R 27/02 204/547 |
| 7,250,115 | B2 | * | 7/2007 | Barth ....................... B82Y 5/00 204/192.34 |
| 7,279,337 | B2 | * | 10/2007 | Zhu ..................... C12Q 1/6825 422/50 |

(Continued)

FOREIGN PATENT DOCUMENTS

| | | | |
|---|---|---|---|
| KR | 1174482 B1 * | 8/2012 | |
| WO | WO 2013056182 A1 * | 4/2013 | ....... G01N 33/48721 |

OTHER PUBLICATIONS

Non-Final Office Action of U.S. Appl. No. 13/893,761 dated Feb. 12, 2016; Robert H. Slick et al.

*Primary Examiner* — Patrick Assouad
*Assistant Examiner* — Sean Curtis
(74) *Attorney, Agent, or Firm* — Boyle Fredrickson, S.C.

(57) ABSTRACT

A piezoelectric substrate having a nanopore opening that separates two reservoirs of conductive fluid may provide for sensitive biological measurements by allowing control of the size of the nanopore according to piezoelectric stimulation of the substrate. Multiple embodiments are provided of monolithic piezoelectric substrates and nanopores for this purpose as well as a control system for controlling the nanopore dimensions electrically using AC or DC waveforms.

15 Claims, 5 Drawing Sheets

(56) References Cited

U.S. PATENT DOCUMENTS

| | | | | |
|---|---|---|---|---|
| 8,039,250 | B2* | 10/2011 | Peng | C12Q 1/6869 435/287.2 |
| 8,246,799 | B2* | 8/2012 | Oliver | G01N 33/48721 204/403.01 |
| 8,247,214 | B2* | 8/2012 | Sowerby | B26F 1/00 210/321.6 |
| 8,262,879 | B2* | 9/2012 | Oliver | G01N 33/48721 204/450 |
| 8,702,948 | B2* | 4/2014 | Ronaghi | B01L 3/502761 204/400 |
| 2002/0006357 | A1 | 1/2002 | McGeoch et al. | |
| 2002/0108869 | A1 | 8/2002 | Savtchenko | |
| 2002/0144905 | A1 | 10/2002 | Schmidt | |
| 2006/0240543 | A1 | 10/2006 | Folch et al. | |
| 2007/0020146 | A1* | 1/2007 | Young | G01N 33/48721 422/82.01 |
| 2007/0138132 | A1* | 6/2007 | Barth | B82Y 5/00 216/56 |
| 2008/0149832 | A1* | 6/2008 | Zorn | B82Y 35/00 250/311 |
| 2010/0188109 | A1* | 7/2010 | Edel | B82Y 15/00 324/693 |
| 2010/0240543 | A1 | 9/2010 | Liotta et al. | |
| 2010/0327255 | A1* | 12/2010 | Peng | B82Y 10/00 257/9 |
| 2011/0045582 | A1 | 2/2011 | Lee et al. | |
| 2011/0111179 | A1* | 5/2011 | Blick | B23K 26/18 428/172 |
| 2012/0049696 | A1* | 3/2012 | Cha | H01L 41/183 310/367 |
| 2012/0057163 | A1* | 3/2012 | Cheng | B82Y 15/00 356/445 |
| 2012/0060589 | A1* | 3/2012 | Gridelet | G01N 33/5438 73/61.61 |
| 2012/0193231 | A1* | 8/2012 | Afzali-Ardakani | G01N 33/48721 204/451 |
| 2012/0193237 | A1* | 8/2012 | Afzali-Ardakani | B82Y 15/00 204/627 |
| 2012/0225435 | A1* | 9/2012 | Seger | B82Y 5/00 435/7.1 |
| 2013/0161194 | A1* | 6/2013 | Jeon | G01N 27/3278 204/606 |
| 2013/0186757 | A1* | 7/2013 | Reinhart | C12Q 1/6869 204/452 |
| 2013/0240378 | A1* | 9/2013 | Lee | G01N 33/48721 205/792 |
| 2013/0249530 | A1* | 9/2013 | Blick | B23K 26/18 324/71.1 |
| 2013/0256137 | A1* | 10/2013 | Holt | G01N 33/48721 204/601 |
| 2013/0264206 | A1* | 10/2013 | Eom | C12Q 1/68 204/452 |
| 2014/0008225 | A1* | 1/2014 | Jeon | G01N 27/44791 204/452 |
| 2014/0021047 | A1* | 1/2014 | Shim | G01N 27/44791 204/451 |
| 2014/0152330 | A1* | 6/2014 | Afzali-Ardakani | B82Y 30/00 324/693 |
| 2014/0158540 | A1* | 6/2014 | Ohura | G01N 33/48721 204/543 |
| 2014/0227679 | A1* | 8/2014 | Lee | B03C 1/01 435/5 |
| 2014/0315328 | A1* | 10/2014 | Lee | G01N 33/54326 436/501 |
| 2015/0010935 | A1* | 1/2015 | Lindsay | G01N 33/48721 435/23 |

\* cited by examiner

SYSTEM AND APPARATUS FOR NANOPORE SEQUENCING

STATEMENT REGARDING FEDERALLY SPONSORED RESEARCH OR DEVELOPMENT

--

CROSS REFERENCE TO RELATED APPLICATION

Background of the Invention

The present invention relates to a system for the direct sequencing of polymers such as DNA and RNA by passing the polymer through a nanoscale pore and measuring an electrical signal modulated by the polymer passing through the pore.

Genetic information may be encoded in a molecule of deoxyribonucleic acid (DNA) as a sequence of nucleotides: (guanine, adenine, thymine, and cytosine). Discovering the sequence of these nucleotides in DNA and other similar molecules is a foundational technology in biological studies.

One promising method of sequencing is "nanopore sequencing" in which a single strand of DNA, forming half of the DNA helix, is passed through a nanoscale opening in a membrane between two reservoirs. This nanopore opening may, for example, be a protein channel held in a lipid bilayer. An electrical potential applied across the reservoirs produces an ion flow between the reservoirs pulling the strand of DNA through the nanopore. As the strand passes through the nanopore, it modulates the ion current though the nanopore as a function of the size of the nucleotide instantaneously obstructing the nanopore. This fluctuation in the ion current may then be analyzed to determine the nucleotide sequence. An example system of nanopore sequencing is described in PCT patent WO2008102120 entitled: Lipid Bilayer Sensor System, hereby incorporated by reference.

The electrical signals produced by changes in ion current through a nanopore with different nucleotides are very small in amplitude and short in time span. For this reason, it can be hard to obtain reliable measurements having sufficient resolution to distinguish between different molecules in the sequence.

SUMMARY OF THE INVENTION

The present invention provides a nanopore whose dimensions may be controlled by electric signal. The ability to adjust the nanopore dimensions, in turn, allows the speed of passage of a polymer through the nanopore to be controlled. By controlling and varying the speed of passage of the polymer, the trade-off between signal quality and processing speed may be better controlled, providing, for example, longer measurement time when a nucleotide is in position within the nanopore and faster transition time between nucleotides.

The nanopore size may be controlled through the use of a piezoelectric substrate experiencing mechanical strain in the presence of a controlled electrical field. In some embodiments, shear strain is used to change a diameter of the nanopore. In some embodiments, the substrate may be operated in a resonant mode or may be controlled based on the signal from the measured polymer.

Specifically, the present invention provides an apparatus for the study of biological molecules that provides a piezoelectric substrate positionable between reservoirs of conductive fluid and presenting a nanopore opening. At least one electrode pair is provided to apply an electrical field to the piezoelectric substrate to change the dimension of the piezoelectric substrate holding the nanopore and at least one electrical sensor measuring a change in the electrical environment of the nanopore.

It is thus a feature of one embodiment of the invention to provide an electrically controllable nanoscale pore useful, for example, for biological measurements related to the passage of materials through the pore.

The piezoelectric substrate may be quartz.

It is thus a feature of at least one embodiment of the invention to provide a piezoelectric substrate material amenable to accepting small holes, for example, possible by laser ablation, and further providing good electrical and mechanical characteristics.

The nanopore may be an ion channel in a membrane suspended across an opening in the piezoelectric substrate and wherein the change in the dimension of the piezoelectric substrate changes a dimension of the membrane holding the nanopore.

It is thus a feature of at least one embodiment of the invention to permit investigations using biological nanopores.

The electrode pair may be positioned on opposite sides of the substrate outside of the reservoirs.

It is thus a feature of at least one embodiment of the invention to permit piezoelectric stimulation of the substrate while removing possibly interfering electrical voltages used for that stimulation from a measurement region around the nanopore.

The nanopore may be provided by a non-piezoelectric material coating an inner surface of an opening in the piezoelectric substrate thus reducing the diameter.

It is thus a feature of at least one embodiment of the invention to provide a nanopore mechanically and directly attached to a piezoelectric substrate eliminating the need for substantial preparation of the substrate before use.

The non-piezoelectric material may include first and second electrically independent sensing electrodes across the nanopore communicating with the electrical sensor.

It is thus a feature of at least one embodiment of the invention to closely integrate sensing electrodes for inductive, capacitive or resistive sensing into the nanopore structure.

The electrodes may provide a change in dimension of the piezoelectric substrate to change at least one diameter of the nanopore.

It is thus a feature of at least one embodiment of the invention to permit a change in nanopore diameter such as may be used to moderate the passage of molecules through the nanopore or for size/charge discrimination of poly-disperse molecules, for example in the case of exonuclease incorporation with DNA.

The electrical field may produce a shear of the substrate along a plane of the substrate.

It is thus a feature of at least one embodiment of the invention to permit nanopore diameter control using electrodes positioned laterally away from the nanopore at readily accessible upper and lower positions.

The apparatus may include multiple electrode pairs positioned on opposite sides of the nanopore providing countervailing thickness shear on opposite sides of the nanopore.

It is thus a feature of at least one embodiment of the invention to enhance the diameter control of the nanopore through the use of opposed shear modes.

The electrodes may be electrically insulated from the piezoelectric material and from the reservoirs.

It is thus a feature of at least one embodiment of the invention to reduce electrical interference between the piezoelectric control electrodes and the sensitive measurements in the region of the nanopore.

The electrical sensor may be any one or combination of a current sensor measuring ion flow through the nanopore as obstructed by the molecules in the nanopore, a capacitance sensor measuring capacitive coupling across the nanopore as changed by different molecules in the nanopore, and a current sensor measuring a resistive flow across the nanopore changed by molecules in the nanopore.

It is thus a feature of at least one embodiment of the invention to provide a versatile system that may use one or more different sensing modalities.

The invention may include an electrical controller communicating with the electrodes on the substrate to operate the electrodes to excite the substrate in a mechanical resonant mode of the substrate to provide a periodic change in nanopore dimension.

It is thus a feature of at least one embodiment of the invention to make use of the high mechanical quality factor (Q) of quartz allowing resonant mode operation.

The electrical controller may control a change in dimension of the nanopore over a time period compatible to a time between passages of different molecules through the nanopore. In one embodiment, the electrical controller may communicate with the electrodes on the substrate to increase a measurement time of each molecule and decrease a time between measurements when molecules are passing through the nanopore.

It is thus a feature of at least one embodiment of the invention to make use of control of the nanopore dimensions to change the speed of passage of a polymeric molecule to increase measurement time for each molecule element while minimizing total measurement time for the entire polymer.

These particular features and advantages may apply to only some embodiments falling within the claims and thus do not define the scope of the invention.

DETAILED DESCRIPTION OF THE PREFERRED EMBODIMENT

Figure 1:
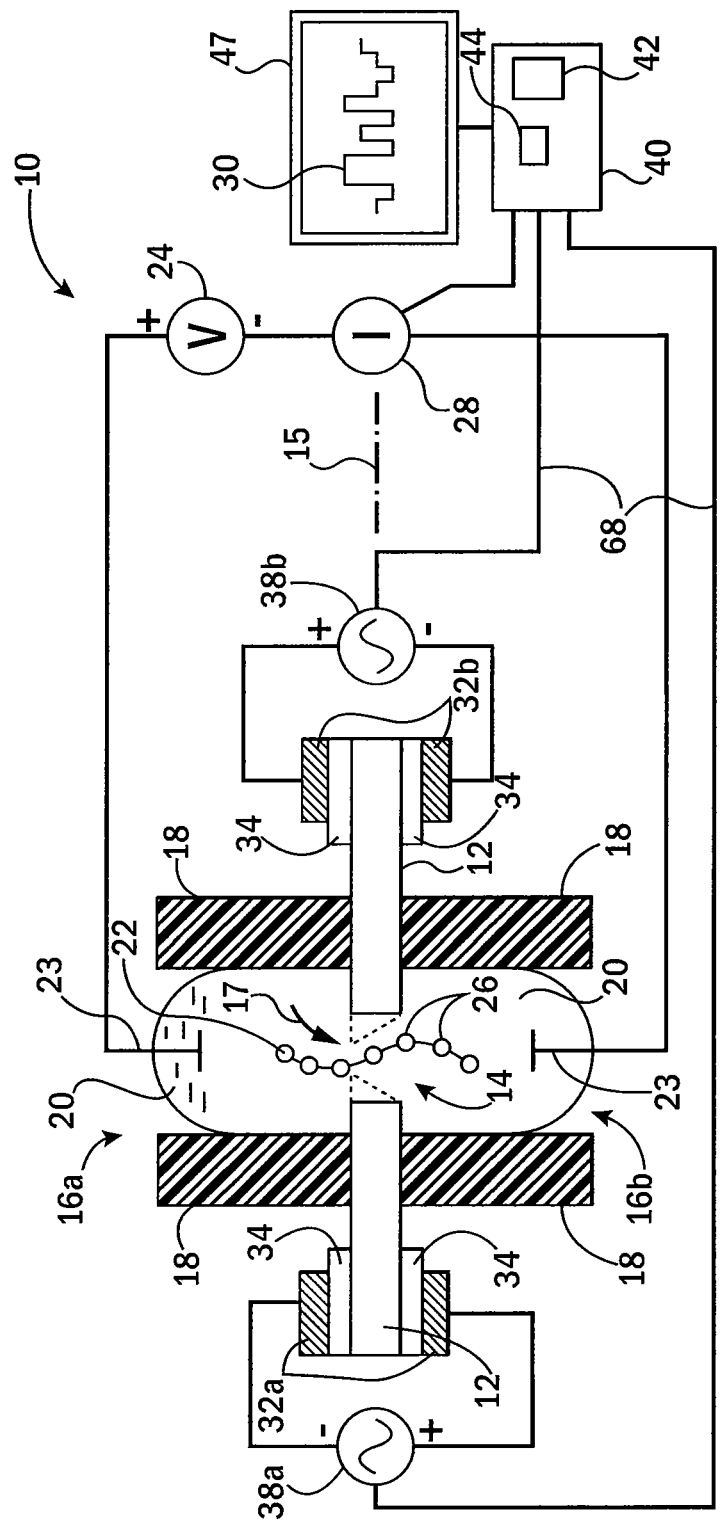
FIG. 1 is a simplified diagram of a nanopore sequencing apparatus providing controllable nanopore dimensions by means of a piezoelectric substrate.

Referring now to FIG. 1, an apparatus 10 for characterizing molecules passing through a nanopore may comprise a generally planar piezoelectric substrate 12 extending along a plane 15 and having an opening 14 passing through the substrate 12 generally perpendicular to the plane 15. A first and second reservoir 16a and 16b may be constructed on either side of the substrate 12 about the opening 14 using upwardly extending and downwardly extending walls so that the reservoirs walls 18 encircle the opening 14 on both sides of the substrate 12. These reservoirs 16a and 16b may be filled with a conductive fluid 20 such as a buffer solution, for example, as held by capillary attraction. Reservoir 16a may have an introduced source of polymer strands 22 (for example, single DNA strands or double strand DNA helices and the necessary proteins and enzymes to separate the helix into strands) suspended therein.

Each of the reservoirs 16a and 16b may provide electrodes 23 communicating with a voltage source 24 together to provide an electrical voltage across the opening 14 tending to produce an ionic flow from reservoir 16a to reservoir 16b. This flow may draw the polymer strands 22 along with it causing individual polymer strands 22 to thread through the opening 14. As monomer units 26 of the polymer strand 22 pass through the opening 14, they may modulate the ionic current through the opening 14 (by blocking ion flow) causing a change in current that may be measured by a sensitive ion current sensor circuit 28. In one embodiment, the ion current sensor circuit 28 may be, for example, a patch clamp amplifier such as the HEKA EPC 10 Signal, commercially available from HEKA Elektronik of GmbH Lambrecht, Germany.

As will be discussed below, other methods of measuring the interaction between the monomer units 26 and the opening 14 may also be used to produce what will be generally termed a modulation signal representing a sensing of the monomer units 26. Each type of monomer unit 26, for example guanine, adenine, thymine, and cytosine in the case of DNA, produces a modulation signal represented as different characteristic current flows which may be analyzed as a time sequence 30 to deduce the sequencing of monomer units 26 in the polymer strand 22.

In the present invention, the substrate 12 may be a single layer of piezoelectric material, for example a quartz material having a thickness of approximately 184 micrometers. The quartz material of substrate 12 may be, in one example, a single AT cut crystal having a resonant frequency of 10 megahertz providing a monolithic and substantially homogenous piezoelectric substrate. Alternatively the substrate 12 may be a laminate of different materials, for example, a silicon layer bonded to a quartz substrate, the latter as described above, using the techniques discussed in 'Bonding Silicon-On-Insulator to Glass Wafers for Integrated Bio-Electronic Circuits', H. S. Kim, R. H. Blick, D. M. Kim, C. B. Eom, Applied Physics Letters 85, 2370 (2004).

The opening 14 may be formed by a laser ablation system, for example, of the type described in U.S. patent application Ser. No. 12/614,237 filed Nov. 6, 2009, assigned to the same assignee as the present invention and hereby incorporated by reference in its entirety. Using this technique, an ultraviolet absorbent liquid is confined to the back side of a quartz substrate to absorb energy when pulsed by an excimer laser passing through the substrate. This increasing energy is accompanied by a jump in temperature and pressure at the liquid/substrate interface inducing pore formation through the quartz substrate. A region around the pore becomes decrystallized and non-piezoelectric but nevertheless the bulk piezoelectric properties of the substrate generally are preserved. This technique may provide for an opening with a diameter as small as 200 nm, while resulting in an end-of-procedure surface roughness of merely tens of nanometers as measured from the respective surface(s) of the substrate 12 such as may provide a gigaohm seal against the cellular membrane. Such hole formation is a result of a simple manufacturing process. Multiple openings 14 and reservoir walls 18 may be placed on a single substrate 12.

Outside of the reservoir walls 18, electrode pairs 32a and 32b may be applied adjacent to the upper and lower surfaces of opposite sides of the substrate 12 about an opening 14 but insulated from the substrate by insulation layers 34. The inventors have determined that displacing the electrode pairs 32 from the opening 14 reduces interference between electrical power applied to the electrode pairs 32 and the measurement of ion current sensor circuit 28 to an acceptable amount consistent with electrical measurements of the modulating effects of the polymer strand 22. The insulation layers 34 may, for example, be provided by a portion of a block of polydimethylsiloxane (PDMS) into which the electrode pairs 32 are embedded.

Each of the electrode pairs 32a and 32b may be generally excited by separate waveform generators 38a and 38b each providing an electrical field that may reach in amplitude of, for example, $5.2 \times 10^6$ V/m. The signals produced by the waveform generators 38a and 38b (or the polarity of the electrode pairs 32a and 32b) may have a phase difference of 180 degrees so as to provide electrical fields that cause a countervailing or opposing shearing distortion of the substrate 12 along plane 15 on opposite sides of the opening 14. This countervailing distortion serves to increase change in a diameter of the opening 14 as a function of the electrical field applied and is shown schematically by means of dotted lines about opening 14. As shown, application of the electrical field reduces the diameter of the opening 14; however, it will be appreciated that the reduction in diameter may occur during a relaxation state when no field is provided. It will be appreciated that other modes of piezoelectric distortion may also be used including face shear, extensional, or longitudinal modes. In particular, it should be noted that the waveform generators 38a and 38b may also operate in a DC mode to statically control the shape and size of the opening 14 and that any AC signal may have a DC offset also allowing static displacement control of the substrate on the sub Angstrom scale.

This change in the size of the opening 14 can be used to moderate the movement of the polymer strand 22 through the opening 14 thereby improving measurement of the monomer units 26. This improvement may be had by delaying passage of the polymer strand 22 when the monomer units 26 are centered in the opening 14 (thereby allowing a longer measurement time and lower signal-to-noise ratio) or may be used in other ways, for example, to control the size of the opening 14 to comport with the size of the monomer unit 26 to enhance sensitivity and linearity of the measurement, or to phase adjust a resonance of the substrate 12 quasi-statically to simply provide fine tuning of a desired flow rate. These techniques will be described further below.

Generally, the electrical signals produced by each of the waveform generators 38a and 38b may be controlled in strength, periodicity, and wave shape by an electric controller such as a computer 40. The electrical signals provided by the waveform generators 38 may be sinusoidal or square wave or other wave shapes controlled in phase, frequency, and power by the computer 40. The computer may further communicate with the electrodes 23 or other sensors associated with the opening 14, for example allowing it to monitor current flow through the opening 14, allowing for a "trigger" to hold the molecule within the opening 14 once it is captured within the opening 14 as will be described below. The computer 40 may execute a stored program 42 held in a non-transitory state in a computer memory as may be executed by electronic processor 45. The computer 40 may provide for standard input devices including a keyboard and the like (not shown) and standard output devices including a graphics display 47 which may provide a graphic depiction of the time sequence 30, for example.

Figure 2:
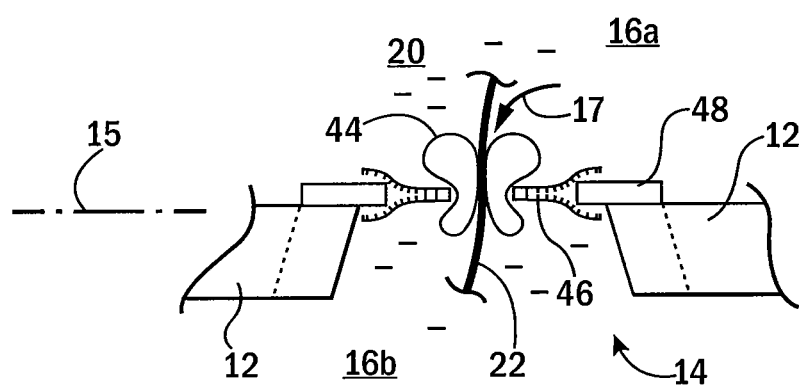
FIG. 2 is a fragmentary detail of the first embodiment of the nanopore employing a protein nanopore supported by the piezoelectric substrate.

Referring now to FIG. 2, in one embodiment, the opening 14 in the substrate 12 may support a protein nanopore 44, the latter held in a lipid bilayer 46 such as a cellular membrane whose periphery is supported by a polymer reservoir 48 adhered to a rim of the opening 14. In this way, the size of the opening 14 may be readily reduced from a larger size generated using laser ablation techniques as described above. Nevertheless, a change in diameter of the opening 14, indicated by dotted lines, provides forces through the polymer reservoir 48 and lipid bilayer 46 received by the protein nanopore 44 to control the inner dimension of the nanopore 44.

Methods of fabricating and assembling of the protein nanopore 44, lipid bilayer 46, and polymer reservoir 48 are described generally in U.S. Pat. No. 8,137,569 and WO/2009077734 hereby incorporated by reference. In this embodiment, opening in the polymer reservoir 48 may be, for example, in the range of one micrometer to 50 micrometers while the opening of the protein nanopore 44 may be on the order of one to 100 nanometers for Alamethicin, however typical nanopore diameters range from a few nanometers to fractions of nanometers, i.e., a few Angstroms. An example protein nanopore 44 may be an Alamethicin ion channel produced by conventional technique as described in the article: Mechanical Actuation of Ion Channels Using a Piezoelectric Planar Patch Clamp System by Eric Stava et al, Lab Chip, 2012, 12, 80 also hereby incorporated by reference. This article also describes an alternative technique suitable for this invention, in which the substrate 12 may be treated to make it hydrophilic and the lipid bilayer 46 attached directly thereto.

Figure 3:
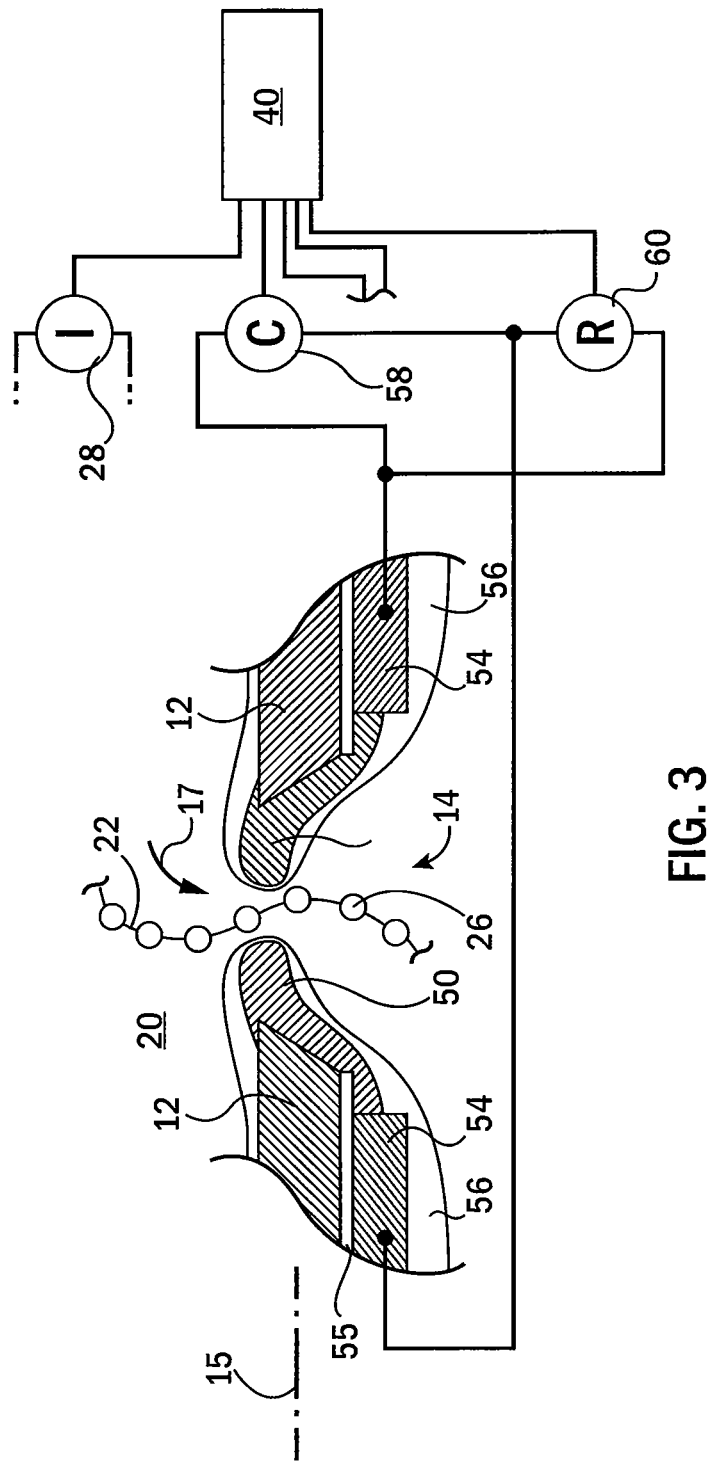
FIG. 3 is a figure similar to FIG. 2 of the second embodiment of the nanopore employing inner measurement electrodes deposited directly on a piezoelectric substrate.
Figure 4A:
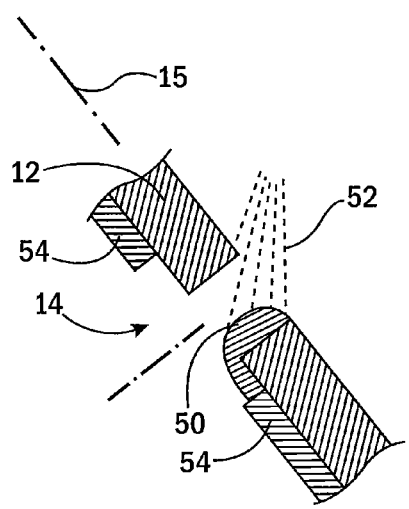
FIGS. 4a and 4b are fragmentary cross-sectional and perspective views respectively of one method of forming measurement electrodes on an opening in a piezoelectric substrate.
Figure 4B:
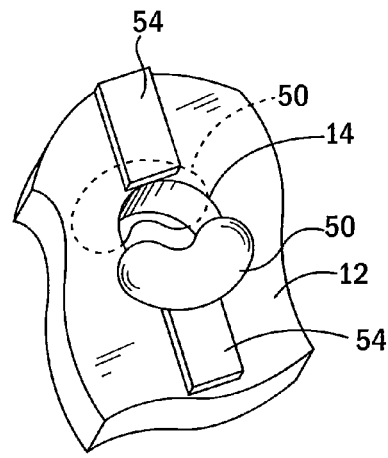

Referring now to FIG. 3, in an alternative embodiment, opening 14 may be narrowed to a nanoscale dimension by the growth of inwardly extending constrictor elements 50 within the opening 14. Referring momentarily to FIGS. 4a and 4b, the constrictor elements 50 may be, for example, deposited by a sputtering or vacuum evaporation process in which a sputtering material 52 such as gold is applied obliquely to the opening 14 to preferentially coat an inner surface of the opening 14 in a radially non-symmetrical way. The substrate 12 may then be rotated by 180 degrees about an axis of the opening 14 and this process repeated to produce two opposed noncontacting and electrically isolated C-shaped constrictor elements 50 together reducing an effective diameter of the opening 14. Desirably, each constrictor element 50 on a given side of the opening 14 may be in electrical communication with a metallic trace 54 on that side of the opening 14. The metallic trace 54 may be insulated from the piezoelectric substrate 12 by a thin insulation layer 55 if desired.

The constrictor elements 50 and traces 54 may be covered with a nonreactive coating 56 for example a thin film of polydimethylsiloxane (PDMS) or parylene (poly(p-xylylene) polymers, further reducing the effective diameter of the opening 14 but preserving a close proximity between the conductive constrictor elements 50 and the strand 22 passing through the opening 14.

This structure of FIG. 3 may be used with the circuitry shown in FIG. 1 to characterize a polymer strand 22 passing through the opening 14 by monitoring ion flow 17. Alternatively or in addition, measurements may be made between traces 54 on opposite sides of opening 14 of capacitive coupling between the constrictor elements 50 and the polymer strand 22 within the opening 14 to provide an alternative method of characterizing the monomer units 26 using a sensitive capacitance measurement circuit 58. This capacitance measurement measures the capacitance between the constrictor elements 50 as modulated by dielectric or conductive properties of the monomer units 26. Alternatively, the capacitance measurement circuit 58 may be replaced or used in addition with a resistance measuring circuit 60 measuring changes in resistance between constrictor elements 50 caused by the interposition of monomer units 26 and relative changes in conduction through the monomer units 26 as opposed to the conductive fluid 20. The measurements provided by each or any of these circuits of the ion current sensor circuit 28, capacitance measurement circuit 58 and resistance measuring circuit 60 may be provided to the computer 40 and used individually or combined for improved signal-to-noise ratio.

Figure 5:
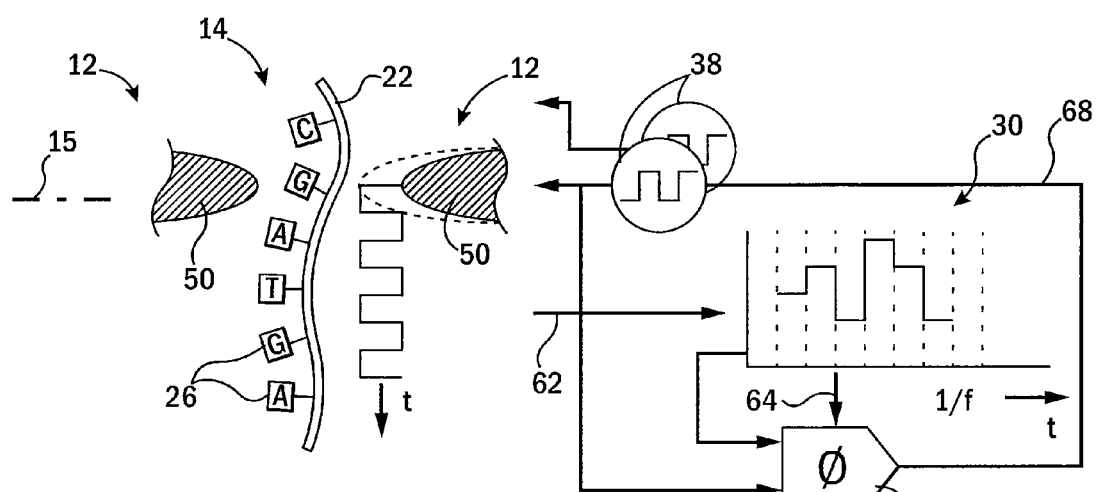
FIG. 5 is a simplified block diagram showing control of the nanopore opening as a function of electrical measurements of nucleotides passing through the nanopore to synchronize the two.

Referring now to FIG. 5, a measurement signal 62 may be derived using any individual or combination of the techniques associated with ion current sensor circuit 28, capacitance measurement circuit 58, or resistance measuring circuit 60 and possibly including other sensor techniques such as optical sensing. This measurement signal 62 may then be analyzed to produce a time sequence 30 described above with respect to FIG. 1 from which a nucleotide sequence may be calculated.

Alternatively or in addition, the measurement signal 62 may be used to control the waveform generators 38 during the movement of the polymer strand 22 through the opening 14.

In one embodiment, the waveform generators 38 may be operated to provide a resonant or periodic excitation to the substrate 12 in which the opening 14 rapidly changes diameter as the polymer strand 22 passes therethrough. This resonant operation may match a natural resonant frequency of the substrate 12 to provide increased diameter variation in the opening 14. Efficient resonant excitation with varying amplitude may also be used with this approach and is facilitated by the single crystal structure of the substrate 12 which gives it a high Q value.

In a more general case, quasi-static or periodic changing of the diameter of the opening 14 may be produced by adjusting a frequency and/or duty cycle of the periodic excitation from the waveform generators 38, and may be used to accurately control the speed of passage of the strand 22 independently or in addition to control of the voltage across the electrodes 23 (shown in FIG. 1).

In one mode of operation, the resonant or non-resonant frequency or amplitude of the output of the waveform generators 38 may be altered to control the dimension of the opening 14 to provide a "ratchet" like action allowing a single monomer unit 26 to pass through the opening 14 in a regular cycle, the opening 14 contracting more closely (on average) about the monomer unit 26 during measurement to prolong the dwell time of the monomer unit 26 within the opening 14 so that ionic current, capacitance or resistance may be stably acquired, and then expanding (on average) about the monomer unit 26 to allow rapid movement to the next monomer unit 26 promoting faster overall processing speed.

For this purpose, a frequency 64 of fluctuations of the time sequence 30 contained in the measurement signal 62 such as indicates a passage of the monomer unit 26 through the opening 14, may be extracted and provided to a phase comparator 66 also receiving output of the waveform generators 38. The phase comparator 66 may output a generator control signal 68 having a phase lock (possibly with different phase offsets) to the time sequence 30 thereby synchronizing opening and closing of the opening 14 with the alignment of monomer units 26 within that opening.

Figure 6:
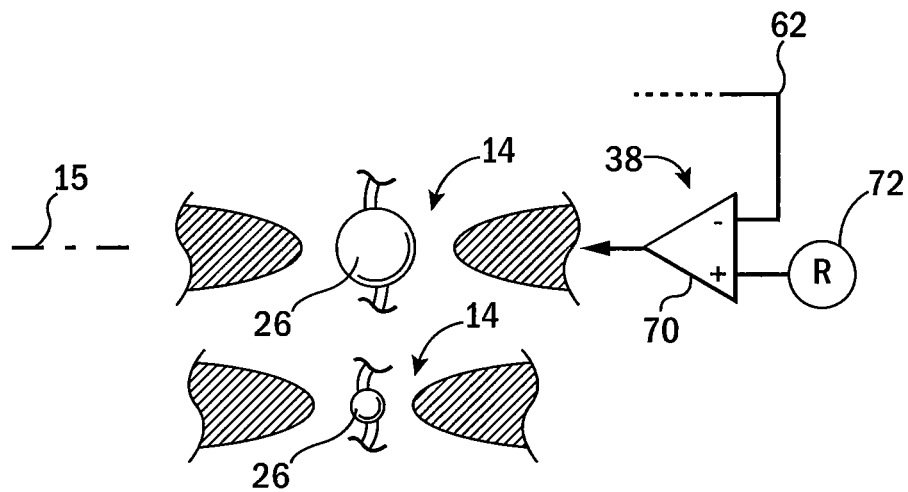
FIG. 6 is a fragmentary block diagram of a second embodiment controlling the nanopore opening as a function of electrical measurement of the nucleotides passing through the nanopore to equalize a sensed electrical signal.

It is contemplated that the present invention in some embodiments may provide for other control techniques that link control of the dimensions of the opening 14 to the measurement signal 62 of the strand 22. For example, as shown in FIG. 6, the static or average diameter of the opening 14 may be controlled by the measurement signal 62 according to a function provided by function block 70, for example a comparator comparing the measurement signal 62 to a reference 72. In this way, for example, the opening 14 may be adjusted according to a size or electrical conductivity of the monomer unit 26 within the opening 14 to provide increased sensitivity or linearization of the measurement such as may be obtained by preserving a more uniform gap between walls of the opening 14 and the monomer units 26.

Figure 7:
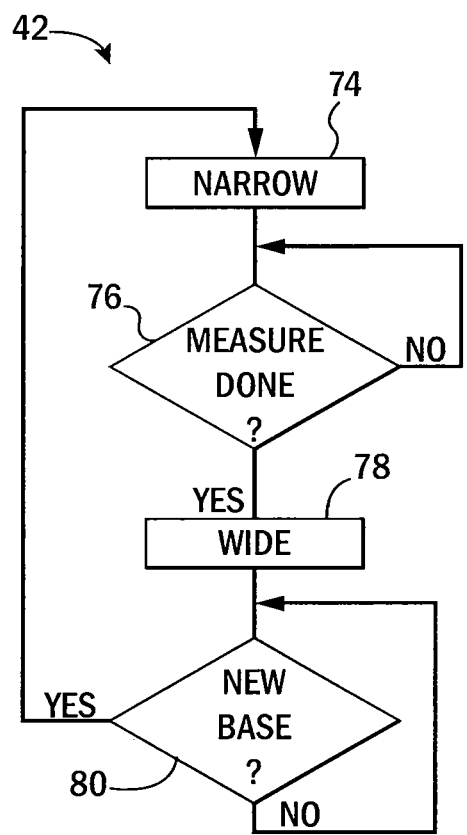
FIG. 7 is a flowchart of a third embodiment of controlling the nanopore opening according to satisfactory completion of the nucleotide measurement.

More generally, and as indicated by FIG. 7, the computer 40 may execute a program providing for a narrowing of the opening 14 as indicated by process block 74 during a measurement until such time that the measurement is complete. Thus, as indicated by decision block 76, when sufficient time has elapsed to obtain a sufficiently low noise measurement of a monomer unit 26 within the opening 14, the program may proceed to process block 78 and the opening 14 widened until a new monomer unit 26 has aligned with the opening, as indicated by decision block 80 detecting an abrupt transition in the time sequence 30.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to a "processor" or "processor unit" should generally be understood to refer broadly to general-purpose computer processing elements for executing stored programs (software) comprised of sequences of arithmetic and logical operations stored in the general-purpose memory. The term "circuit" as used herein should be considered to broadly include both analog and digital circuitry together with associated firmware. The term "program" generally refers to a sequence of operations executed by a processor or circuit.

References to memory, unless otherwise specified, can combinations of different memory structures including solid-state and electromechanical memories and may describe a distributed system of main memory and multiple cache layers. The term page table should be understood generally relate to a table mapping predefined address blocks of memory between a virtual address space and a physical address space regardless of the exact size of those blocks or the particular name given to the blocks. In all these cases, the guest operating system or hypervisor establish or install the bypass mapping values and the actual bypass is handled by the processing circuitry.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

We claim:

1. An apparatus for a study of biological molecules comprising:
   a piezoelectric substrate positionable between reservoirs of conductive fluid;
   a nanopore opening in the piezoelectric substrate between the reservoirs;
   at least one electrode pair applying an electrical field to the piezoelectric substrate to change a dimension of the piezoelectric substrate holding the nanopore; and
   at least one electrical sensor measuring a change in the electrical environment of the nanopore
   wherein the at least one electrode pair is electrically insulated from the piezoelectric substrate and from the reservoirs.

2. The apparatus of claim 1 wherein at least one electrode pair is displaced outside of an area between the reservoirs.

3. The apparatus of claim 1 wherein the nanopore is provided by a non-piezoelectric material coating an inner surface of an opening in the piezoelectric substrate.

4. The apparatus of claim 3 wherein the non-piezoelectric material includes first and second electrically independent sensing electrodes across the nanopore communicating with the electrical sensor.

5. The apparatus of claim 1 wherein the at least one electrode pair provides a change in dimension of the piezoelectric substrate to change at least one diameter of the nanopore.

6. The apparatus of claim 5 wherein electrical field produces a shear of the substrate along a plane of the substrate.

7. The apparatus of claim 6 including multiple electrode pairs positioned on opposite sides of the nanopore providing countervailing thickness shear on opposite sides of the nanopore.

8. The apparatus of claim 1 wherein the piezoelectric substrate is quartz.

9. The apparatus of claim 1 wherein the at least one electrical sensor is a current sensor measuring ion flow through the nanopore as obstructed by the molecules in the nanopore.

10. The apparatus of claim 1 wherein the at least one electrical sensor is a capacitance sensor measuring capacitive coupling across the nanopore as changed by different molecules in the nanopore.

11. The apparatus of claim 1 wherein the at least one electrical sensor is a current sensor measuring a resistive flow across the nanopore changed by molecules in the nanopore.

12. The apparatus of claim 1 further including an electrical controller communicating with the at least one electrode pair on the substrate to operate the at least one electrode pair to excite the substrate in a mechanical resonant mode of the substrate to provide a periodic change in nanopore dimension.

13. The apparatus of claim 1 further including an electrical controller communicating with the at least one electrode pair on the substrate to operate the at least one electrode pair to provide a change in dimension of the nanopore over a time period compatible to a time between passage of different molecules through the nanopore.

14. The apparatus of claim 1 further including an electrical controller communicating with the at least one electrode pair on the substrate to operate the at least one electrode pair on the substrate as a function of signals received from the at least electrical sensor.

15. The apparatus of claim 1 wherein the at least one electrode pair on the substrate is operated to increase a measurement time of the molecules and decrease a time between measurements when molecules are passing through the nanopore.

* * * * *